US006756031B2

(12) United States Patent
Evans et al.

(10) Patent No.: US 6,756,031 B2
(45) Date of Patent: Jun. 29, 2004

(54) COMPOSITIONS FOR USE IN EMBOLIZING BLOOD VESSELS

(75) Inventors: Scott Evans, Santa Ana, CA (US); Richard J. Greff, St. Pete Beach, FL (US); James I. Wright, Villa Park, CA (US)

(73) Assignee: MicroTherapeutics, Inc., Irvine, CA (US)

( * ) Notice: Subject to any disclaimer, the term of this patent is extended or adjusted under 35 U.S.C. 154(b) by 0 days.

(21) Appl. No.: 10/025,791

(22) Filed: Dec. 26, 2001

(65) Prior Publication Data

US 2002/0076381 A1 Jun. 20, 2002

Related U.S. Application Data

(63) Continuation of application No. 08/917,721, filed on Aug. 27, 1997, now Pat. No. 6,342,202, which is a division of application No. 08/802,252, filed on Feb. 19, 1997, which is a continuation of application No. 08/655,822, filed on May 31, 1996, now abandoned.

(51) Int. Cl.$^7$ .......................... A61K 49/04; A61K 47/32; A61K 47/34; A61K 47/38; A61K 9/08
(52) U.S. Cl. ...................... 424/9.411; 424/423; 424/9.4
(58) Field of Search ........................... 424/9.41, 9.411, 424/423, 486–88, 9.4; 523/105

(56) References Cited

U.S. PATENT DOCUMENTS

| 3,527,224 | A | 9/1970 | Rabinowitz et al. |
| 3,591,676 | A | 7/1971 | Hawkins |
| 4,079,124 | A | 3/1978 | Winchell |
| 4,631,188 | A | 12/1986 | Stoy et al. |
| 4,795,741 | A | 1/1989 | Leshchiner et al. |
| 4,938,763 | A | 7/1990 | Dunn et al. |
| 5,202,352 | A | 4/1993 | Okada et al. |
| 4,938,763 | A | 7/1995 | Dunn et al. |
| 5,443,454 | A | 8/1995 | Tanabe et al. |
| 5,525,334 | A | 6/1996 | Ito |
| 5,580,568 | A | 12/1996 | Greff et al. |
| 5,667,767 | A | 9/1997 | Greff et al. |
| 5,695,480 | A | 12/1997 | Evans |
| 5,702,361 | A | 12/1997 | Evans |

FOREIGN PATENT DOCUMENTS

| JP | 3-252799 | 9/1991 |
| JP | 4-55273 | 3/1992 |
| JP | 4-301502 | 9/1992 |
| JP | 406107549 A | 4/1994 |
| WO | 85/00969 | 3/1985 |
| WO | 97/04656 | 2/1997 |
| WO | 97/04657 | 2/1997 |
| WO | 97/04813 | 2/1997 |

OTHER PUBLICATIONS

Amdur et al., Editors, "Toxic Effects of Metals", *Toxicology*, 4th Edition, pp. 661–664, Pergamon Press, New York, New York.

Chaloupka, John C., et al., "Technical Feasibility and Histopathologic Studies of Ethylene Vinyl Copolymer (EVAL) Using a Swine Endovascular Embolization Model," *American Journal of Neuroradiology*, vol. 15, No. 6, 1994, pp. 1107–1115.

Guglielmi, et al., "Electrothrombosis of Saccular Aneurysms via Endovascular Approach", *J. Neurosurg.*, 75:8–14 (1991).

Kinugasa, et al., "Early Treatment of Subarachnoid Hemorrhage After Preventing Rerupture of an Aneurysm", *J. Neurosurg.*, 83:34–41 (1995).

Kinugasa, et al., "Prophylatic Thrombosis to Prevent New Bleeding and to Delay Aneurysm Surgery", *Neurosurgery*, 36(4):661–667 (1995).

Kinugasa, et al., "Direct Thrombosis of a Pseudoaneurysm after Obliteration of a Carotid–Cavernous Fistula with Cellulose Acetate Polymer: Technical Case Report", *Neurosurgery*, 35(4):755–760 (1994).

Kinugasa, et al., "Direct Thrombosis of Aneurysms with Cellulose Acetate Polymer, Part II: Preliminary Clinical Experience", *J. Neurosurg.*, 77:501–507 (1992).

Link, D.P., et al., "Hydrogel Embolic Agents Theory and Practice of adding Radio–Opacity," *Investigative Radiology*, vol. 29, No. 8, 1994, pp. 746–751.

Mandai, et al., "Direct Thrombosis of An.eurysms with Cellulose Acetate Polymer, Part I: Results on Thrombosis in Experimental Aneurysms", *J. Neurosurg.*, 77:497–500 (1992).

Miyatake, et al., "Cobb's Syndrome and its Treatment with Embolization", *J. Neurosurg.*, 72:497–499 (1990).

Naitoh, et al., "Removal of Beta–2–Microglobulin by Diffusion Alone is Feasible Using Highly Permeable Dialysis Membranes", *Trans Am Soc Artif Intern Organs*, XXXIV:630–634 (1988).

Park, et al., "New Polymers for Therapeutic Embolization", Poster #47, Meeting of Radiological Society of North American (1993).

Sadato, et al., "Experimental Study and Clinical Use of Poly(vinyl acetate) Emulsion as Liquid Embolisation Material", *Neuroradiology*, 36:634–641 (1994).

Stoy, et al., "Injectable Physiologically Acceptable Polymeric Compositions", *International Patent Application Publication No. 85 00969*, published Mar. 14, 1985.

(List continued on next page.)

*Primary Examiner*—Edward J. Webman
(74) *Attorney, Agent, or Firm*—Foley & Lardner LLP

(57) ABSTRACT

Disclosed are compositions suitable for use in embolizing blood vessels which compositions comprise a polymer, a biocompatible solvent and a contrast agent. The polymer is selected from the group consisting of polyacrylonitrile, polyurethane, polyvinylacetate, cellulose acetate butyrate, nitrocellulose and copolymers of urethane/carbonate and copolymers of styrene/maleic acid.

9 Claims, No Drawings

OTHER PUBLICATIONS

Su, et al., Histophathological Studies of a New Liquid Embolization Method Using Estrogen–Alcohol and Polyvinyl Acetate, *Surg. Neurol.* 36(1):4–11 (1991).

Sugiu, et al., "Direct Thrombosis of Experimental Aneurysms with Cellulose Acetate Polymer (CAP): Technical Aspects, Angiographic Follow Up, and Histological Study", *J. Neurosurg.*, 83:531–538 (1995).

Taki, W., et al., "A New Liquid Material for Embolization of Arteriovenous Malformations," *American Journal of Neuroradiology*, vol. 11, No. 1, 1990, pp. 163–168.

Taki, et al., "A New Liquid Material for Embolization of Arteriovenous Malformations", *AJNR*, 11:163–168 (1990).

Taki, et al., "Selection and Combination of Various Endovascular Techniques in the Treatment of Giant Aneurysms", *J. Neurosurg.*, 77:37–42 (1992).

Taki, et al., "Possiblity and Limit of Intravascular Surgery", *Medical Tribune*, pp. 46–47 (1989).

Terada, et al., "Embolization of Arteriovenous Malformations with Peripheral Aneurysms using Ethylene Vinyl Alcohol Copolymer", *J. Neurosurg.*, 75:655–660 (1991).

Yamashita, et al., "Characteristics of Ethylene Vinyl Alcohol Copolymer (EVAL) Mixtures", *AJNR*, 15:1103–1105 (1994).

Castaneda–Zuniga, et al, "Interventional Radiology", in *Vascular Embolotherapy*, Part I, (1), pp. 9–32, William & Wilkins Publishers (1992).

COMPOSITIONS FOR USE IN EMBOLIZING BLOOD VESSELS

CROSS-REFERENCE TO RELATED APPLICATIONS

This application is a continuation of application Ser. No. 08/917,721, filed on Aug. 27, 1997 now U.S. Pat. No. 6,342,202, which was a Divisional application of prior application Ser. No. 08/802,252, filed Feb. 19, 1997, which was a Continuation of prior application Ser. No. 08/655,822 originally filed on May 31, 1996 abandoned.

BACKGROUND OF THE INVENTION

1. Field of the Invention

This invention is directed to novel compositions suitable for use in embolizing blood vessels. In particular, this invention is directed to embolizing compositions comprising a biocompatible polymer, a biocompatible solvent and a contrasting agent. The compositions of this invention find particular utility in embolizing blood vessels in, for example, the treatment of aneurysms and in ablating diseased tissues.

References

The following publications are cited in this application as superscript numbers:

Mandai, et al., "Direct Thrombosis of Aneurysms with Cellulose Acetate Polymer", *J. Neurosurg.*, 77:497–500 (1992)

Kinugasa, et al., "Direct Thrombosis of Aneurysms with Cellulose Acetate Polymer", *J. Neurosurg.*, 77:501–507 (1992)

Greff, et al., U.S. Pat. No. 5,580,568 for "Cellulose Diacetate Compositions for Use in Embolizing Blood Vessels."

Greff, et al., U.S. Pat. No. 5,667,767 for "Novel Compositions for Use in Embolizing Blood Vessels."

Evans, et al., U.S. Pat. No. 6,103,254 for "Methods for the Reversible Sterilization of Male Mammals."

Evans, et al., U.S. Pat. No. 5,989,580 for "Methods for the Reversible Sterilization of Female Mammals."

All of the above references are herein incorporated by reference in their entirety to the same extent as if each individual reference was specifically and individually indicated to be incorporated herein by reference in its entirety.

2. State of the Art

It is desirable in many clinical situations to embolize blood vessels to prevent/control bleeding (e.g., organ bleeding, gastrointestinal bleeding, vascular bleeding, bleeding associated with an aneurysm) or to ablate diseased tissue (e.g., tumors, etc.). Embolization of blood vessels has heretofore employed certain polymer compositions and particulates, e.g., silicone, metallic coils, sclerosing materials and the like. Because of their ease in delivery, water insoluble non-biodegradable polymers such as cellulose acetate[1,2,3] or ethylene vinyl alcohol[4] dissolved in, for example, DMSO have been employed to embolize blood vessels. These compositions are delivered to the vascular site to be embolized by, for example, a catheter or a syringe. Typically, these compositions will comprise a contrast agent to facilitate guidance of the catheter or syringe to the vascular site as well as the placement of the polymer precipitate which embolizes the blood vessel. Upon contact with the aqueous blood environment at this vascular site, the DMSO dissipates away from the insoluble polymer which results in polymer precipitation and embolization of the blood vessel.

In addition to use in embolizing blood vessels, these compositions can also be employed in the reversible sterilization of mammalian males and females.[5,6] In the former case, the polymer composition is injected into the vas deferens and upon contact with the aqueous fluid therein, precipitates to block the vas. In the latter case, the polymer composition is injected into the fallopian tubes and upon contact with the aqueous fluid therein, precipitates to block the tube. In either case, sterilization arising from the blockage can be reversed at a latter date by injecting DMSO into the polymer blockage to remove the polymer.

While progress has been made in the development of compositions which can be employed in such methods, only a limited number of polymers suitable for use in such compositions have been identified. While these polymers minimally meet the criteria for use in these environments, the identity of additional polymers is essential to developing versatile methods utilizing the specific characteristics of each polymer. For example, embolization techniques requiring deep vascular penetration will require a composition having a relatively slow polymer precipitation rate. Contrarily, techniques requiring rapid embolization of, for example, a bleeding aneurysm or a high blood flood vascular site will require a composition having a relatively fast polymer precipitation rate.

In either case, polymers suitable for use in such compositions must meet stringent conditions for use in embolizing blood vessels, in reversible sterilization, etc. Specifically, suitable polymers ideally should be soluble in the biocompatible solvent, be easy to deliver (e.g., low viscosity) via a catheter or a syringe, be compatible with a contrast agent, and the resulting precipitate should form a well defined coherent mass which is non-biodegradable. This last requirement is, of course, essential to use in vivo where a coherent mass is critical to either successful embolization or sterilization. Likewise, compatibility with the contrast agent is necessary in order to permit monitoring the in vivo injection of the composition and to confirm its presence after the procedure is complete.

SUMMARY OF THE INVENTION

This invention is directed to the discovery of novel polymers which are suitable in compositions useful in in vivo applications such as in embolizing blood vessels and/or reversibly sterilizing mammalian patients. Specifically, this invention is directed to the discovery that polymers such as polyacrylonitrile, polyvinylacetate, cellulose acetate butyrate, nitrocellulose and copolymers of urethane/carbonate and copolymers of styrene/maleic acid can be employed in combination with a biocompatible solvent and a contrast agent and the resulting compositions are suitable for use in embolizing blood vessels, in reversible sterilization of mammalian patients, etc.

Accordingly, in one of its composition aspects, this invention is directed to a composition comprising:

(a) from about 2.5 to about 8.0 weight percent of a polymer selected from the group consisting of polyacrylonitrile, polyvinylacetate, cellulose acetate butyrate, nitrocellulose and copolymers of urethane/carbonate and copolymers of styrene/maleic acid, and mixtures thereof;

(b) from about 10 to about 40 weight percent of a contrast agent;

(c) from about 52 to about 87.5 weight percent of a biocompatible solvent;

wherein the weight percent of the polymer, contrast agent and biocompatible solvent is based on the total weight of the complete composition.

In one of its method aspects, this invention is directed to a method for embolizing a blood vessel by injecting into said blood vessel a sufficient amount of a composition comprising:

(a) from about 2.5 to about 8.0 weight percent of a polymer selected from the group consisting of polyacrylonitrile, polyvinylacetate, cellulose acetate butyrate, nitrocellulose and copolymers of urethane/carbonate and copolymers of styrene/maleic acid, and mixtures thereof;

(b) from about 10 to about 40 weight percent of a contrast agent;

(c) from about 52 to about 87.5 weight percent of a biocompatible solvent wherein the weight percent of the polymer, contrast agent and biocompatible solvent is based on the total weight of the complete composition under conditions wherein a precipitate is formed which embolizes the blood vessel.

In a preferred embodiment, the contrast agent is a water insoluble contrast agent. In still a further preferred embodiment, the biocompatible solvent is dimethylsulfoxide (DMSO).

DETAILED DESCRIPTION OF THE INVENTION

This invention is directed to novel compositions comprising specific polymers, a contrast agent and a biocompatible solvent.

Prior to discussing this invention in further detail, the following terms will first be defined:

The term "embolizing" as used in conjunction with "embolizing compositions" and "embolizing agents" refers to a process wherein a material is injected into a blood vessel which thereafter fills or plugs the blood vessel and/or encourages clot formation so that blood flow through the vessel ceases. The embolization of the blood vessel is important in preventing/controlling bleeding (e.g., organ bleeding, gastrointestinal bleeding, vascular bleeding, bleeding associated with an aneurysm) or to ablate diseased tissue (e.g., tumors, etc.) by cutting off its blood supply.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a particle size of about 10 $\mu$m or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the male mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the vas deferens fluid. Preferably, the biocompatible solvent is dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that the contrast agent and copolymer form an integral coherent precipitate which does not separate into a copolymer component and a contrast agent component.

The term "hydrocarbyl" refers to organic residues comprising only carbon and hydrogen atoms which residues include, by way of example, alkyl, aryl, alkylaryl, arylalkyl, alkenyl, etc. The hydrocarbyl group typically contains from 1 to 12 carbon atoms.

Compositions

The compositions of this invention are prepared by conventional methods whereby each of the components is added and the resulting composition mixed together until the overall composition is substantially homogeneous. Specifically, sufficient amounts of the selected polymer are added to the biocompatible solvent to achieve the effective concentration for the complete composition. Preferably, the embolizing composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

The polymers suitable for use in this composition include, by way of example, polyacrylonitrile, polyvinylacetate, cellulose acetate butyrate, nitrocellulose and copolymers of urethane/carbonate and copolymers of styrene/maleic acid, and mixtures of such polymers. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7.

In any event, the polymers typically will have a molecular weight of at least about 50,000 and more preferably from about 75,000 to about 300,000. In a particularly preferred embodiment, the molecular weight of the polymer can be selected relative to the desired viscosity of the resulting composition. It being understood, of course, that polymers of higher molecular weight will provide for a higher viscosity in the composition as compared to the same polymer having a lower molecular weight.

Sufficient amounts of the contrast agent are then added to the biocompatible solvent to achieve the effective concentration for the complete composition. Preferably, the composition will comprise from about 10 to about 40 weight percent of the contrast agent and more preferably from about 20 to about 40 weight percent and even more preferably 35 weight percent. Insofar as the contrast agent is not soluble in the biocompatible solvent, stirring is employed to effect homogeneity of the resulting suspension. In order to enhance formation of the suspension, the particle size of the contrast agent is preferably maintained at about 10 $\mu$m or less and more preferably at from about 1 to about 5 $\mu$m (e.g., an average size of about 2 $\mu$m). In one preferred embodiment, the particle size of the contrast agent is prepared, for example, by fractionation. In such an embodiment, a water insoluble contrast agent such as tantalum having a particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under a microscope. The process is optionally repeated until a desired particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Methods

The compositions described above can then be employed in methods for embolizing mammalian blood vessels or for reversible sterilization of mammalian patients. In the case of blood vessel embolization, a sufficient amount of this composition is introduced into the selected blood vessel by conventional means (e.g., injection or catheter delivery under fluoroscopy) so that upon precipitation, of the polymer, the blood vessel is embolized. The particular amount of embolizing composition employed is dictated by the total volume of the vasculature to be embolized, the concentration of polymer in the composition, the rate of precipitation (solids formation) of the polymer, etc. Such factors are well within the skill of the art. In the case of the copolymers recited above, the rate of precipitation can be controlled by changing the overall hydrophobicity/hydrophilicity of the polymer with faster precipitation rates being achieved by a more hydrophobic polymer composition. In this regard, increasing the amount of butyrate content (at the expense of the acetate content) in the cellulose acetate butyrate will also increase the hydrophobicity of the polymer.

One particularly preferred method for delivering the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

When delivered by catheter, the injection rate dictates, in part, the form of the precipitate at the vascular site. Specifically, low injection rates of approximately 0.05 to 0.3 cc/minute will provide for a precipitate in the form of a kernel or nodule which is particularly beneficial for site specific embolization because the precipitate forms primarily at the point of injection. Contrarily, high injection rates of about 0.1 to 0.5 or more cc/several seconds (e.g., up to 10 seconds) will provide for a filament like mass projecting downstream from the catheter tip which may be particularly beneficial for providing the embolizing agent deep into the vascular tree. Such procedures are suitable for embolizing tumor masses, organs and arteriovenous malformations (AVM).

When introduced into the vascular site, the biocompatible solvent diffuses rapidly into the blood and a solid precipitate forms which precipitate is the water insoluble polymer with the contrast agent encapsulated therein. Without being limited to any theory, it is believed that initially, a soft gel to spongy solid precipitate forms upon contact with the blood. This precipitate then restricts blood flow, entrapping red cells thereby causing clot embolization of the blood vessel.

Utility

The compositions described herein are useful in embolizing mammalian blood vessels which, in turn, can be used-to prevent/control bleeding (e.g., organ bleeding, gastrointestinal bleeding, vascular bleeding, bleeding associated with an aneurysm) or to ablate diseased tissue (e.g., tumors, etc.). Accordingly, these compositions find use in human and other mammalian subjects requiring embolization of blood vessels.

Additionally, these compositions can be used in the reversible sterilization of mammalian patients as described in concurrently filed applications by Evans, et al.[5,6].

It is contemplated that these compositions can be employed as a carrier for a compatible pharmaceutically active compound wherein this compound is delivered in vivo for subsequent release. Such compounds include by way of example only antibiotics, anti-inflammatory agents, chemotherapeutic agents, and the like.

The following examples are set forth to illustrate the claimed invention and are not to be construed as a limitation thereof.

EXAMPLES

Unless otherwise stated, all temperatures are in degrees Celsius. Also, in these examples, unless otherwise defined below, the abbreviations employed have their generally accepted meaning:

| | |
|---|---|
| cc = | cubic centimeter |
| cps = | centipoise |
| DMSO = | dimethylsulfoxide |
| gm = | gram |
| mL = | milliliter |
| RT = | room temperature |

Example 1

The purpose of this example is to determine the suitability of different polymers in compositions comprising DMSO and a contrast agent. The tests were conducted as follows:

1. 1.2 grams of a candidate polymer was weighed out and placed into a 20 mL bottle that had a Teflon capliner in the lid.
2. 12.5 mL (13.8 gm) DMSO was added to the bottle containing the candidate polymer and the cap was placed onto the vial tightly.

3. Each of the bottles was placed in a tightly sealed half gallon jar and placed in an oven at 50° C.
4. The bottles were maintained in the oven for approximately 72 hours and thereafter were allowed to cool to RT.
5. Once the samples reached RT, they were visually examined to determine if the polymers were soluble in DMSO.
6. The viscosity of each of the soluble polymers was then estimated relative to a 100 cps fluid standard. All viscosities reported are for 20° C.
7. Each of the dissolved polymer solutions was drawn into a syringe and then injected into a physiological saline solution through a 20 gauge blunt needle to determine whether a coherent precipitate formed.

In this example, 21 different polymer compositions were evaluated and the results are set forth in Table I below.

TABLE I

| Polymer | Dissolve | Coherent Precipitate | Viscosity (cps) |
|---|---|---|---|
| polymethyl methacrylate | YES | YES (brittle) | <100 |
| polybutyl methacrylate | PARTIAL | — | — |
| poly(acrylic acid-co-maleic acid) Na | NO | — | — |
| polyacrylonitrile | YES | YES (strong) | >100 |
| poly(ethylene-co-methacrylic acid) Na | NO | — | — |
| poly(acrylamide-co-acrylic acid) | NO | — | — |
| polycarbonate | NO | — | — |
| poly(carbonate-urethane) | YES | YES (rubbery) | ~100 |
| polyurethane | NO | — | — |
| polyamide (Nylon 6 or 66) | NO | — | — |
| poly(ethylene-co-vinyl acetate) | PARTIAL | — | — |
| polysulfone | PARTIAL | — | — |
| poly(vinylacetate) | YES | YES (weak) | <100 |
| cellulose acetate butryate | YES | YES (weak) | <100 |
| polyester | NO | — | — |
| polyester | NO | — | — |
| silicone resin | YES | NO (flock) | <50 |
| nitrocellulose | YES | YES (weak) | >100 |
| poly(styrene-co-maleic acid) | YES | YES (weak) | <100 |
| poly(vinylpyrrolidone co-vinyl acetate) | YES | NO (liquid) | <100 |
| poly(methyl vinyl ether-co-maleic acid | YES | NO (liquid) | >100 |

The above results indicate that of the 21 polymers tested, only 11 were soluble in DMSO and of the 11 only 8 formed precipitates in the saline solution. Of these 8, the brittleness of the polymethyl methacrylate precludes its use in embolizing compositions. Accordingly only 6 of the polymers tested are suitable for use in this invention. These six polymers were as follows: polyacrylonitrile, polyvinylacetate, cellulose acetate butyrate, nitrocellulose and copolymers of urethane/carbonate and copolymers of styrene/maleic acid. Certain polymers provide properties which are more advantageous in certain environments over others.

Example 3

The purpose of this example is to illustrate how an in vivo application of the methods of this invention in the sterilization of a male mammal could be accomplished. In this example, a 50 pound male dog is prepared for sterilization using a composition comprising 5.8 weight percent polyacrylonitrile (PAN) and 20 weight percent tantalum in DMSO. This composition is loaded into a syringe having a needle attached thereto. Local procaine anaesthesia is applied to the scrotum area of the subject. The vas deferens of one side is gripped through the skin by a vas-fixation clamp and lifted. The syringe needle is used to puncture the vas in the direction away from the testis. The PAN polymer composition (0.3 cc) is then delivered to the lumen of the vas deferens. The delivery is easily visualized with fluoroscopy due to the presence of a contrast agent in the polymer composition. After delivery, the DMSO in the PAN composition rapidly diffuses and the PAN precipitates in the lumen resulting in a blockage of the vas deferens. After about 5 minutes, the polymer is fully precipitated and the syringe needle is removed from vas.

The same procedure is repeated with the other vas deferens of the male subject.

Example 4

The purpose of this example is to illustrate an in vivo embolization using a composition of this invention.

In this example, a 50 pound male hound was prepared for blood vessel embolization using a composition comprising 5.8 weight percent poly(carbonate-urethane) 20 weight percent tantalum in DMSO was loaded into a syringe. Embolization of the left kidney proceeded by placement of a 3F micro catheter into the kidney through a 5F AngioDynamics Headhunter catheter. The catheter was advanced into the renal artery, flushed with contrast agent to identify the location and then flushed with saline, followed by DMSO, followed by 0.3 cc of the composition described above. The composition was quickly injected into the renal artery over several seconds. After delivery of about 0.2 cc of the composition, the upper pole of the kidney was blocked. Delivery of the remaining composition resulted in the entire kidney being embolized.

The above results indicate that the compositions of this invention are suitable for in vivo embolization of blood vessels in mammalian subjects.

From the foregoing description, various modifications and changes in the composition and method will occur to those skilled in the art. All such modifications coming within the scope of the appended claims are intended to be included therein.

What is claimed is:

1. A composition comprising:
   (a) from about 2.5 to about 8.0 weight percent of a polymer selected from the group consisting of polyacrylonitrile, polyvinylacetate, cellulose acetate butyrate, nitrocellulose and copolymers of urethane/carbonate and copolymers of styrene/maleic acid, and mixtures thereof wherein said polymer has a molecular weight of at least 50,000;
   (b) from about 10 to about 40 weight percent of a contrast agent wherein said contrast agent is tantalum or tantalum oxide;
   (c) from about 52 to about 87.5 weight percent of dimethylsulfoxide which solubilizes said polymer; and
   wherein the weight percent of the polymer, contrast agent and biocompatible solvent is based on the total weight of the complete composition.

2. The composition according to claim 1 wherein said contrast agent is tantalum.

3. The composition according to claim 1 wherein said contrast agent is tantalum oxide.

4. The composition according to claim 1 wherein said polymer is polyacrylonitrile.

5. The composition according to claim 1 wherein said polymer is polyvinylacetate.

6. The composition according to claim 1 wherein said polymer is cellulose acetate butyrate.

7. The composition according to claim 1 wherein said polymer is nitrocellulose.

8. The composition according to claim 1 wherein said polymer is a copolymer of urethane/carbonate.

9. The composition according to claim 1 wherein said polymer is a copolymer of styrene/maleic anhydride.

* * * * *